United States Patent [19]

Takasaki

[11] Patent Number: 5,316,924
[45] Date of Patent: May 31, 1994

[54] PULLULANASE, METHODS OF PRODUCING PULLULANASE AND METHODS OF SACCHARIFICATION OF STARCH USING PULLULANASE

[75] Inventor: Yoshiyuki Takasaki, Miyazaki, Japan

[73] Assignee: Research Development Corporation of Japan, Japan

[21] Appl. No.: 890,518

[22] Filed: May 28, 1992

[30] Foreign Application Priority Data

Feb. 28, 1992 [JP] Japan .................. 4-043336

[51] Int. Cl.$^5$ ............ C12P 21/00; C12P 19/16; C12N 9/44
[52] U.S. Cl. .................. 435/71.2; 435/98; 435/210
[58] Field of Search ............ 435/98, 210, 252.1, 435/822, 71.2

[56] References Cited

U.S. PATENT DOCUMENTS

| | | | |
|---|---|---|---|
| 3,560,345 | 2/1971 | Yokobayashi et al. | 435/210 |
| 3,565,765 | 2/1971 | Heady et al. | 435/95 |
| 3,654,082 | 4/1972 | Abdullah | 435/98 |
| 3,716,455 | 2/1973 | Ueda et al. | 435/210 |
| 3,741,873 | 6/1973 | Ueda et al. | 435/188 |
| 3,790,446 | 2/1974 | Gunja-Smith | 435/98 |
| 3,827,940 | 8/1974 | Sugimoto et al. | 435/210 |
| 3,963,575 | 6/1976 | Bulich | 435/98 |

FOREIGN PATENT DOCUMENTS

| | | |
|---|---|---|
| 0063909 | 11/1982 | European Pat. Off. . |
| 60-54679 | 3/1985 | Japan . |
| 60-188065 | 9/1985 | Japan . |
| 1230545 | 5/1971 | United Kingdom . |
| 1260418 | 1/1972 | United Kingdom . |
| 1336599 | 11/1973 | United Kingdom . |
| 2097405A | 11/1982 | United Kingdom . |

OTHER PUBLICATIONS

M. Abdullah and D. French, Arch. Biochem. Biophys., 137: 483–493 (1970), "Substrate Specificity of Pullulanase".

K. Kainuma et al., Biochem. Biophys. Acta, 410: 333–346 (1975), "Purification and Some Properties of a Novel Maltohexose-Producing Exo-Amylase from Aerobacter Aerogenes".

B. E. Norman, Starch/Stärke 34: 340–346 (1982), "A Novel Debranching Enzyme for Application in the Glucose Syrup Industry".

J. F. Robyt and R. J. Ackerman, Arch. of Biochem and Biophys., 145: 105–114 (1971); "Isolation, Purification and Characterization of a Maltotetraose-Producing Amylase from *Pseudomonas stutzeri*".

N. Saito, Arch. of Biochem. and Biophys., 155: 290–298 (1973), "A Thermophilic Extracellular α-Amylase from *Bacillus lichenformis* ".

Y. Takasaki, Agr. Biol. Chem., 40 (8): 1523–1530 (1976), "Purifications and Enzymatic Properties of β-Amylase and Pullullanase from *Bacillus cerus* var. mycoides".

Y. Takasaki, Agric. Biol. Chem., 46 (6): 1539–1547 (1982) "Production of Maltohexaose by α-Amylase from Bacillus Circulans G-6".

(List continued on next page.)

Primary Examiner—Robert J. Warden
Assistant Examiner—Robert Carpenter
Attorney, Agent, or Firm—Pennie & Edmonds

[57] ABSTRACT

The present invention provides a novel pullulanase, methods of producing and isolating the pullulanase and methods of saccharifying starch using the pullulanase. The pullulanase of the invention works in a wide pH range, as large as pH 4–9. In addition, the pullulanase is heat stable and its optimum temperature is about 60° C. Therefore, the pullulanase of the invention can be used in the saccharification of starch along with amylase, which is enzymatically active at pH 4–9, to increase the yield of saccharides.

1 Claim, 1 Drawing Sheet

OTHER PUBLICATIONS

Y. Takasaki, Agric. Biol. Chem., 49(4): 1091–1097 (1985), "An Amylase Producing Maltotriose from *Bacillus subtilis*".

Y. Takasaki, Agric. Biol. Chem., 51 (1): 9–16 (1987) "Pullulanase-Amylase Complex Enzyme from *Bacillus subtilis*".

Y. Takasaki et al., Agric. Biol. Chem., 55 (7): 1715–1720 (1991), "Maltotetraose-producing Amylase from Bacillus sp. MG-4".

Y. Takasaki et al., Agric. Biol. Chem., 55 (3): 687–692 (1991), "Maltotriose-producing Amylase from *Microbacterium imperiale*".

S. Ueda and N. Nanri, Applied Microbiol., 15 (3): 492–499 (1967), "Production of Isoamylase by *Escherichia intermedia*".

S. Ueda et al., J. Ferment Technol., 49 (6): 552–558 (1971), "Production of Isoamylase by Streptomyces sp. No. 28".

G. J. Walker, Biochem. J., 108: 33–40 (1968), "Metabolism of the Reserve Polysaccharide of *Streptococcus mitis*".

PULLULANASE, METHODS OF PRODUCING PULLULANASE AND METHODS OF SACCHARIFICATION OF STARCH USING PULLULANASE

The present invention relates to novel pullulanase, methods of producing the pullulanase and methods of saccharifying starch using the pullulanase.

BACKGROUND OF THE INVENTION

Pullulanase is an enzyme that hydrolyzes α-1, 6-glucosidic bond of pullulan to eventually produce maltotriose. Recently, pullulanase has drawn a special attention due to its enzymatic ability to remarkably increase the production of various saccharides: pullulanase is used along with glucoamylase (optimum pH: 4.5, optimum temperature: 60° C.) to improve the yield of glucose from starch; pullulanase is used along with soybean β-amylase [optimum pH: about 6, optimum temperature: 55°-60° C., Enzyme and Food Processing ed. by G. G. Brich, Applied Science Publishers Ltd., London, 73-88 (1981) Japanese Patent Application Kokoku 37849/1971 etc.] or bacterial β-amylase [optimum pH: about 7, optimum temperature; about 50° C., Y. Takasaki, Agric. Biol, Chem., Vol. 40, No. 8, 1523 (1976) etc.] to obtain higher yield of maltose from starch; pullulanase is used along with enzymes (each of them has optimum pH: about 7-8, optimum temperature: 55°-60° C.) which are produced by bacteria belonging to genus Bacillus etc. to improve the yield of maltooligosaccharides such as maltotriose, [Y. Takasaki, Agric. Biol. Chem., Vol. 49, No. 4, 1091 (1985) etc.] maltotetraose [J. F. Robyt et. al., Arch. Biochem., Biophys., Vol. 145, 105 (1971), Y. Takasaki, Agric. Biol. Chem., Vol. 55, No. 7, 1715 (1991) etc.] maltopentaose [N. Saito, Arch. Biochem. Biophys., Vol. 155, No. 290 (1978) etc.] and maltohexaose [K. Kainuma et. al., J. Biochem. Biophy. Acta, Vol. 410, 333 (1975), Y. Takasaki, Agric. Biol. Chem., 46, 1589 (1982) Fermentation and Industry, Vol. 40, 477 (1983) etc.].

The working pH of these amylase used along with pullulanase is in the range of as large as 4-8 so that pullulanase is required to be enzymatically active in the same pH range for the production of saccharides. In addition, the enzyme should be heat stable, for example, at least 55°-60° C., during reaction to prevent the contamination of microorganisms, and should be used for a long period of time at that temperature for the industrial application of the enzyme.

It has been known that pullulanase is produced by many kinds of bacteria such as those belonging to genus Aerobacter [*Aerobacter aerogenes* (*Klebsiella pneumoniae*), H. Bender and K. Wallenfels, Biochem. Z. Vol. 334, 79(1961), M. Abdullah, Arch. Biochem. Biophys., Vol. 137, 483 (1970) etc.], Streptomyces [S. Ueda et. al., J. Ferment. Tech., Vol. 49, 552 (1971) etc.], Streptococcus [*Streptococcus mitis*, G. W. Walker, Biochem. J., Vol. 108, 33 (1968) etc.], Escherichia [*Escherichia intermedia*, S. Ueda et. al. Applied Microbiol., Vol. 15, 492 (1967), U.S. Pat. No. 3,716,455(1973) etc.], Bacillus [Japanese Patent Application Kokoku 25036/1987, 25037/1987, Agric. Biol. Chem. Vol. 40, No.8, 1523 (1976) K. Horikoshi Japanese Patent Application Kokoku 27786/1978 etc.], Flavobacterium [*Flavobacterium esteromaticum*, Japanese Patent Application Kokoku 18826/1973], Cytophaga [U.S. Pat. No. 3,790,446 (1974), Lactobasillus, Micrococcus, Nocardia, Staphylococcus, Azotobactger, Sarcina etc. [England Patent 11260418, U.S. Pat. No. 3,827,940 (1974)] and Actinomycetes [Norcardia, Micromonospora, Thermomonospora, U.S. Pat. No. 3,741,873 (1973)].

Most of the pullulanase known in the art are not heat stable and its optimum temperature is 40°-50° C. Even if pullulanase is heat stable, it has problem in pH: the working pH of a pullulanase is limited in an acidic side (optimum pH: 5) and the pullulanase does not work at neutral pH (e.g., pullulanase produced by bacteria belonging to the genus Bacillus [Japanese patent application kokoku Sho 62-25036, 62-25037]; the working pH of a pullulanase is limited at around neutral pH and the pullulanase does not work at acidic side (e.g., pullulanase produced by bacteria belonging to the genus Streptomyces [J. Ferment. Tech., Vol. 49, 552 (1971) etc.]). These pullulanase for one reason or another have characteristics which are not favorable as an all-purpose pullulanase for industrial use.

SUMMARY OF THE INVENTION

The pullulanase of the invention is enzymatically active in a wide pH range and heat stable. The pullulanase of the invention can be used along with glucoamylase produced by *Aspergillus niger* in the same condition, a combination which promotes saccharification of liquefied starch and gives an increased yield of glucose. In addition, the pullulanase of the invention can be used along with β-amylase or various oligosaccharide-producing amylase to efficiently produce various oligosaccharides.

DETAILED DESCRIPTION OF THE INVENTION

Figure 1:
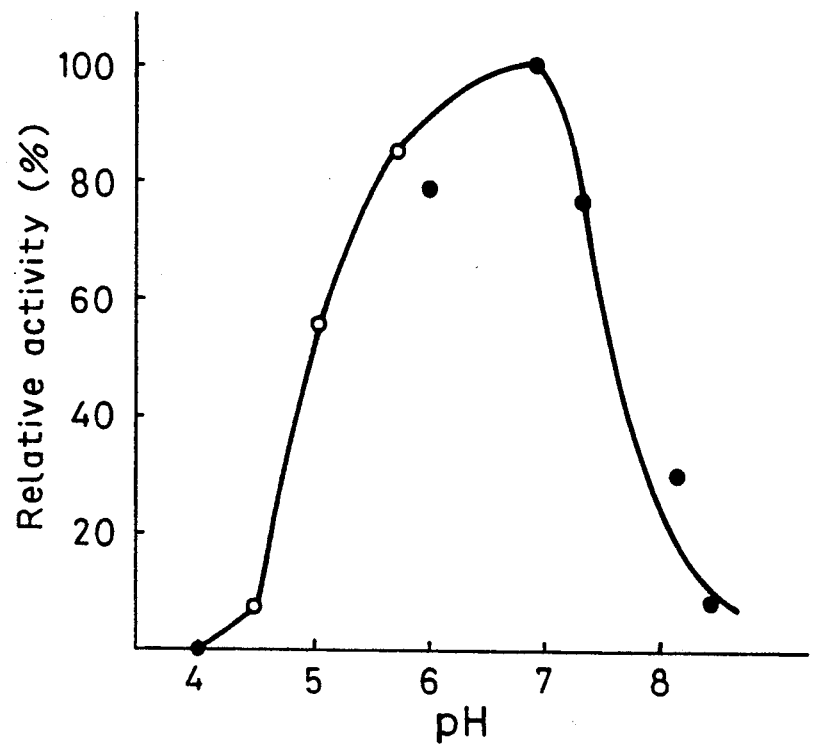
FIG. 1 shows an optimum pH of pullulanase of the present invention. Symbol —○— indicates that acetate buffer is used for reaction and symbol —●— indicates that phosphate buffer is used for reaction.

The present inventors have attempted to find bacteria capable of producing pullulanase that is heat stable, active in a wide pH range and useful for production of various saccharides from starch. We have found that certain bacterium belonging to the genus Microbacterium isolated from soil produces a significant amount of pullulanase and extracellularly secretes the enzyme and that the enzyme has the suitable properties described above.

There has been no report so far that bacteria belonging to the genus Microbacterium produce pullulanase.

In the conventional method of producing glucose from starch, starch liquified with α-amylase produced by bacteria belonging to the genus Bacillus is saccharified with glucoamylase produced by microorganisms belonging to the genus Aspergillus or Rhizopus.

Although glucoamylase hydrolyzes both the α-1,4-glucosidic bond and α-1,6-glucosidic bond of amylopectin, the hydrolysis activity is not strong enough on the α-1,6-glucosidic bond and takes time. In addition, the enzyme catalyzes the reverse reaction to form isomaltose and panose making it difficult to achieve glucose yields of greater than 95% glucose. These properties of glucoamylase prevent a saccharification yield from attaining more than 95%.

In the saccharification of starch in which glucoamylase is used, the saccharification is promoted in the presence of an enzyme, for example, pullulanase, that hydrolyzes the α-1,6-glucosidic bond of amylopectin, and the increased saccharification in turn increases the production of glucose. Such methods in which the yield of glucose is increased by using a combination of pullulanase and glucoamylase are disclosed in the following: T. I. Hurst et. al., have used pullulanase produced by bacteria belonging to the genus Aerobacter (*Aerobacter aerogenes* pullulanase, U.S. Pat. No. 3,897,306/1975, Japanese Patent Application Kokoku No. 29570/1979, 50/1982); the present inventors (genus Bacillus pullulanase, Japanese Patent Application Kokoku Nos. 39/1982, 14159/1982) and K. K. Nealsens, B. E. Norman et. al. [*Bacillus acidopullulyticus* pullulanase, Japanese Patent Application Kokoku Nos. 25036/1987, 25037/1987 (Japanese Patent Application Kokai 174089/1982). Starch, Vol. 34, 340 (1982)].

Glucoamylase produced by *Aspergillus niger* has an optimum pH of around 4.5 and an optimum temperature of 60° C. An enzyme used along with glucoamylase is required to be enzymatically active in the same condition. It has been known that pullulanase enzymatically active in the above-condition is produced by bacteria belonging to the genus Bacillus (Japanese Patent Application KOKOKU Nos. 25036/1987, 25037/1987, KOKAI No. 84485/1988), and the pullulanase is utilized to produce glucose. The enzyme is not enzymatically active at around neutral pH and is not suitable to be used with α-amylase whose optimum pH is 6.5–8 to produce oligosaccharides.

Figure 2:
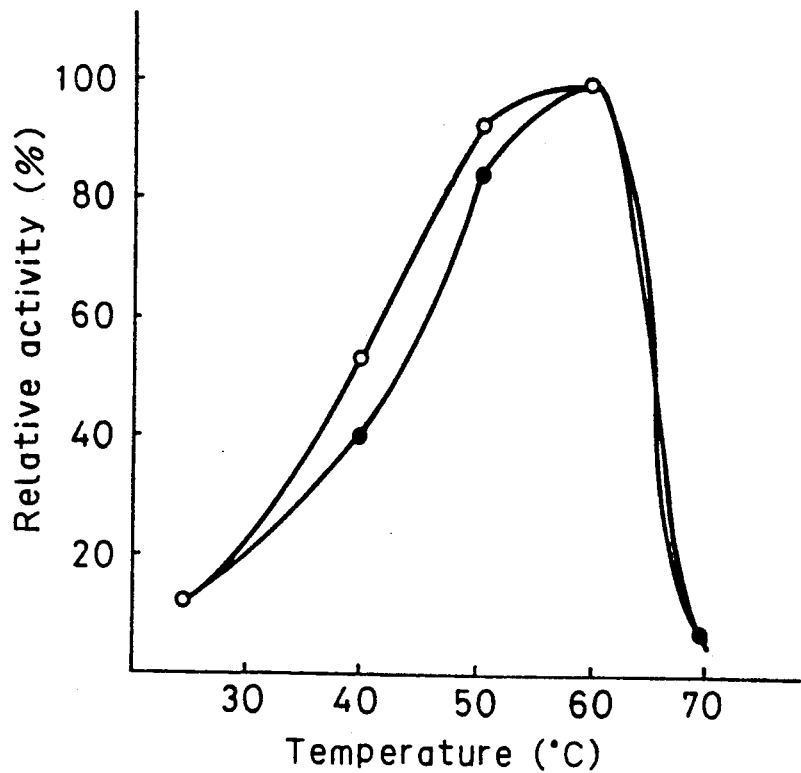
FIG. 2 shows an optimum temperature of pullulanase of the present invention. Symbol —●— indicates that acetate buffer/pH5.0 is used for reaction and symbol —○— indicates that phosphate buffer/pH7.0 is used for reaction. The pullulanase of the invention is reacted with 1% pullulan in acetate or phosphate buffer at pH5 or 7 for 30 minutes.

The present invention provides a pullulanase having the following characteristics:

a) Action and substrate specificity;

The pullulanase hydrolyzes the α-1,6-glucosidic bond of pullulan to produce maltotriose and also hydrolyzes the α-1,6-glucosidic bond of amylopectin and its derivatives.

b) Working pH and Optimum pH;

The pullulanase has a working pH of 4–9 and an optimum pH of 6.5–7.5 at 60° C. when the pullulanase is reacted with 1% pullulan in 0.1M acetate buffer or 0.1M phosphate buffer at 60° C. for 30 minutes, and the pullulanase still works well at an acidic-side pH, such as pH of below 5 (see FIG. 1).

c) Working temperature and optimum temperature;

The pullulanase has an optimum temperature of about 60° C. when reacted with 1% pullulan as a substrate in acetate buffer (pH5) or phosphate buffer (pH7) for 30 minutes (see FIG. 2).

d) pH-stability;

The pullulanase maintains about 90% or more enzymatic activity in acetate buffer or phosphate buffer at pH4.5–10, after three-hour treatment at 30° C.

e) Heat stability;

The pullulanase is inactivated by about 10% at 50° C., by about 30% at 55° C. or by about 60% at 60° C. when a pullulanase solution is heated for 10 minutes. However, the pullulanase is stabilized in the presence of a substrate (liquified starch) and $Ca^{2+}$. For example, the pullulanase is not inactivated after treated in the presence of $1 \times 10^{-2}$M $CaCl_2$ at 50° or 55° C. for 10 minutes.

f) Stabilization;

The pullulanase is stabilized in the presence of cations such as $Ca^{2+}$, $Sr^{2+}$ and $Ba^{2+}$ that protect the pullulanase from heat inactivation.

g) Inhibitors;

The pullulanase is inhibited by $Cu^{2+}$, $Fe^{2+}$ and $Hg^{2+}$ etc.

The pullulanase of the present invention is purified and analyzed as follows.

Purification

A culture supernatant is treated as follows:
(1) Adsorbed using a calcium phosphate gel,
(2) Eluted with 0.5M $K_2HPO_4$,
(3) Precipitated with ammonium sulfate (70% saturated),
(4) Subjected to DEAE-Sepharose column chromatography and Bio-gel column chromatography,
(5) The purified pullulanase showed a single band on electrophoresis.

Activity measurement

An enzymatic activity is measured as follows,
(1) 1% pullulan in 0.1M phosphate buffer, 7.0 pH is prepared,
(2) the enzyme solution is added to 0.5 ml of (1)
(3) Distilled water is added to bring a final volume of 1.0 ml.
(4) Reaction is carried out at 60° C.,
(5) Reaction product is quantitatively analyzed by Somogyi-Nelson method.
Definition: 1 unit of an enzyme is defined by an amount of enzyme that produces 1 μmol glucose for one minute under the assay conditions.

The pullulanase of the present invention is produced by a method which comprises culturing in a culture medium bacteria belonging to the genus Microbacterium capable of producing pullulanase, producing and accumulating pullulanase in the culture medium and recovering the pullulanase from the culture.

The bacterium of the present invention belonging to the genus Microbacterium, isolated from soil, has the following bacteriological properties.

(1) Morphology: Rod (about 10 μm × 40 μm), —shows polymorphism according to culture conditions, changing from rod to cocci form.
(2) Oxygen demand: obligate aerobe
(3) Gram staining: +
(4) Spore: —
(5) Motility: +
(6) Flagella: peritrichous
(7) Oxidase: +
(8) Catalase: +
(9) OF test: F
(10) Generation of gas from-glucose:
(11) Presence of mesodiaminopimelic acid in the hydrolyzed whole cell: —
(12) Degradation of starch: +
(13) Degradation of cellulose: —
(14) Gelatin liquefaction: +
(15) Reduction of nitrate: +
(16) Degradation of urea: —
(17) Color of colony: yellow
(18) Citric acid utilization: +
(19) Generation of hydrogen sulfide: —
(20) Formation of acids from saccharides:

shows +for D-glucose, D-fructose, D-galactose, D-mannose, lactose, maltose, cellobiose, dextrin, starch shows −for inulin, inositol, L-sorbose, L-rhamnose, raffinose The bacterium of the invention was identified as *Microbacterium imperiale* by Bergey's Manual of Determinative Bacteriology Volume 7 and 8, according to the properties described above. The bacterium was deposited on Feb. 24, 1992 with Fermentation Research Institute, Agency of Industrial Science and Technology, Ministry of International Trade and Industry of 1-3, Higashi 1-chome, Tsukuba-shi, Ibaraki-ken, 305 Japan and was assigned the accession number FERM BP-3761.

To produce the pullulanase of the invention by culturing the bacterium, a culture medium comprises a nitrogen and carbon source and salts. The nitrogen source includes organic materials such as defatted soybean, corn steep liquor, meat extract, peptone, milk casein, yeast extract and fish meal. Among them, corn steep liquor, soy protein, defatted soybean and fish meal are an especially suitable nitrogen source. Additionally, an inorganic nitrogen source such as ammonium sulfate, ammonium chloride, urea and ammonium nitrate may be supplementarily used, if necessary.

The carbon source typically includes starch and its derivatives such as starch, liquefied starch, and dextrin, or pullulan. In addition to the nitrogen and carbon source, phosphate, magnesium salts, sodium salts, potassium salts, manganese salts, molybdate are used as a supplement. The addition of phosphate, magnesium salts, iron salts, zonc salts and copper salts is especially beneficial. Preferably, 0.05-0.5% potassium diphosphate ($K_2HPO_4$) as a phosphate, 0.05-0.3% $MgSO_4 \cdot 7H_2O$ as a magnesium salt, $1 \times 10^{-6}$ $1 \times 10^{-5}M$ manganese sulfate as a manganese, $1 \times 10^{-3} - 1 \times 10^{-2}M$ calcium chloride as a calcium salt, $1 \times 10^{-6} - 1 \times 10^{-4}M$ ferrous sulfate as an iron salt and $1 \times 10^{-6} - 1 \times 10^{-4}M$ copper sulfate as a copper salt may be added.

The pullulanase of the invention is active in a wide pH range, heat stable and useful for efficiently saccharifying starch and its derivatives in the presence of glucoamylase, β-amylase, or oligosaccharide-producing α-amylase.

The pullulanase of the invention is stable in acidic side and heat stable and can be used along with glucoamylase produced by *Aspergillus niger* or *Rhizopus delemar* which is commercially available: the pullulanase can be used to promote saccharification of liquefied starch at 55°-65° C., pH4.5-5.5 to give an increased yield of glucose. For example, 0.1-0.5 unit of pullulanase of the present invention per 1 g of a substrate is added to 30-35% liquefied starch for saccharification. The yield of glucose increases 0.5-2% and a saccharified solution containing 95-97% glucose is obtained.

As is evident from FIG. 1, the pullulanase of the invention has a wider pH range than the pullulanase known in the art. In a combination with β-amylase (optimum pH6-8) produced by plants or bacteria belonging to the genus Bacillus, the pullulanase of the invention can be used to efficiently produce maltose from liquefied starch. Alternatively, in a combination with various maltooligosaccharide-producing enzymes (optimum pH6-8), the pullulanase of the invention can be used to efficiently produce various maltooligosaccharides.

EXAMPLE

The present invention is further described by Examples, which are not intended to limit the scope of the invention.

EXAMPLE 1

30 ml of a culture medium (5% soy protein, 0.3% fish meat extract, 0.6% corn steep liquor, 0.3% $K_2HPO_4$, 0.1% $MgSO_4 \cdot 7H_2O$, 0.3% urea, 2% soluble starch, 0.1% sodium dodecyl sulfate, 0.5% NaCl, $5 \times 10M^{-5}$ $CuSO_4$, $1.5 \times 10M^{-6}$ $MnSO_4$, $1 \times 10^{-3}M$ $CaCl_2$, $1 \times 10^{-4}M$ $ZnSO_4$, $1 \times 10^{-5}M$ $FeSO_4$)/pH 7 was placed in a 200-ml erlenmeyer flask, sterilized and inoculated with *Microbacterium imperiale* (FERM BP-3761). The bacterium was cultured with shaking (225 rpm) at 30° C. A certain amount of the culture was taken periodically during the culture. The sample was centrifuged and the supernatant was tested for pullulanase activity.

TABLE 1

| Cultivation time | final pH | Growth of bacteria ($OD_{660}$ nm) | Amount of pullulanase (units/ml broth) |
|---|---|---|---|
| 24 | 6.7 | 10.3 | 2.5 |
| 67 | 7.2 | 20.5 | 8.7 |
| 90 | 8.6 | 38.1 | 12.8 |
| 114 | 8.8 | 31.1 | 15.1 |

As is evident from Table 1, 15.1 unit of pullulanase/1 ml of culture was produced in a 114-hour cultivation.

EXAMPLE 2

50 ml of a culture medium (10% corn steep liquor, 0.3% $K_2HPO_4$, 0.1% $MgSO_4 \cdot 7H_2O$, 2% lactose, 0.1% Tween40, $1 \times 10^{-2}M$ $CaCl_2$)/pH 6 was placed in a 200-ml erlenmeyer flask, sterilized and inoculated with *Microbacterium imperiale* (FERM BP-3761). The bacterium was cultured with shaking at 30° C. for four days. A certain amount of the culture was taken periodically during the culture. The sample was centrifuged and the supernatant was tested for pullulanase activity. 22.3 unit of pullulanase/1 ml of culture was produced.

EXAMPLE 3

The pullulanase obtained in Example 1 was used along with maltotriose-producing amylase (produced by AMANO PHARMACEUTICAL Co.) to produce maltotriose.

1 unit of pullulanase per 1 g of a substrate and 1 unit of maltotriose-producing amylase per 1 g of a substrate were added to 10% liquefied starch (DE, dextrose equivalent 4.2). The reaction mixture was incubated at 50° C., pH7 for 2 days. After the reaction, the reaction product was quantitatively analyzed for saccharides composition by high pressure liquid chromatography. Table 2 shows the results.

TABLE 2

| Pullulanase | Yield of maltotriose (%) |
|---|---|
| Not-Added | 61.2 |
| Added | 71.1 |

As is evident from Table 1, the pullulanase of the invention increased the yield of maltotriose by about 10%.

EXAMPLE 4

The pullulanase obtained in Example 1 was used along with glucoamylase produced by *Aspergillus niger* to saccharify liquified starch.

About 30% liquefied starch (DE 7.7), $5 \times 10^{-2}$M acetate buffer/pH 4.6 or 5.0, $1 \times 10^{-2}$M $CaCl_2$, glucoamylase (0.2 unit/g substrate) were combined. The mixture was incubated in the presence or absence of pullulanase (0.5 unit/g substrate) at 60° C. for 30 hours. After the reaction, the reaction product was quantitatively analyzed for a saccharide composition by high pressure liquid chromatography. Table 3 shows the results.

TABLE 3

| Pullulanase | pH | \multicolumn{4}{c}{Yield of glucose (%)} |
|---|---|---|---|---|---|
| | | 22 (hour) | 25 (hour) | 30 (hour) | 36 (hour) |
| Not added | 4.6 | 93.4 | 94.5 | 95.1 | 95.0 |
| Not added | 4.8 | 91.8 | 92.9 | 94.1 | 93.7 |
| 0.5 unit/g substrate | 4.6 | 93.7 | 95.4 | 96.2 | 96.3 |
| 0.5 unit/g substrate | 4.8 | 96.5 | 96.8 | 96.7 | 96.5 |

As is evident from Table 3, when pullulanase was not added, the yield of glucose was a maximum of 95.1%. In contrast, the yield of glucose was 96.3% or 96.8% when pullulanase was added. 1 unit of a glucoamylase is defined by an amount of enzyme that produces 1 μM glucose for one minute from 1% soluble starch (containing $5 \times 10^{-2}$M acetate buffer) at 40° C., pH 5.0.

EXAMPLE 5

Instead of glucoamylase produced by *Aspergillus niger*, glucoamylase produced by *Rhizopus delemar* was used.

About 33.5% liquefied starch (DE 8.5), $5 \times 10^{-2}$M acetate buffer/pH 5.3, $1 \times 10^{-2}$M $CaCl_2$, glucoamylase (6.0 unit/g substrate) were combined. The mixture was incubated in the presence or absence of pullulanase (0.5 unit/g substrate) at 55° C. for 48 hours. When pullulanase was not added, the yield of glucose was 94.5%. In contrast, the yield of glucose was 95.4% when pullulanase was added.

Several references have been cited in the specification, the entire disclosure of each of which are incorporated herein in their entirety by reference. This application claims priority benefits under 35 U.S.C. §119 of Japan Patent Application No. 43336/1992 filed Feb. 28, 1992, the entire disclosure of which is incorporated herein by reference.

What is claimed is:

1. A method of producing pullulanase comprising:
   (a) culturing in a culture medium the bacterium, accession number Ferm BP-3761, or mutants thereof *Microbacterium imperiale* capable of producing said pullulanase wherein the pullulanase has the following characteristics:
      i) a working pH of 4–9;
      ii) an optimum temperature of about 60° C.;
      iii) a pH stability of pH 4.5–10; and
      iv) being inactivated by about 10% at 50° C., by about 30% at 55° C. or by about 60% at 60° C. when a solution containing pullulanase is heated for 10 minutes; and
      v) not being inactivated when a pullulanase solution containing $1 \times 10^{-2}$M $CaCl_2$ is heated at 50° or 55° C. for 10 minutes;
   b) allowing the pullulanase to accumulate in the culture medium; and
   c) isolating the pullulanase from the culture medium.

* * * * *